United States Patent [19]

Matsumoto

[11] 4,092,344

[45] May 30, 1978

[54] CYCLOHEXENYL RESORCINOL DERIVATIVES

[75] Inventor: Ken Matsumoto, Indianapolis, Ind.

[73] Assignee: Eli Lilly and Company, Indianapolis, Ind.

[21] Appl. No.: 761,745

[22] Filed: Jan. 24, 1977

Related U.S. Application Data

[62] Division of Ser. No. 638,019, Dec. 5, 1975, abandoned.

[51] Int. Cl.$^2$ ............... C07C 39/17; C07C 43/22; C07C 69/76; C07C 121/75
[52] U.S. Cl. ............... 260/465 F; 260/333; 260/343.41; 260/520 R; 260/559 R; 260/613 R; 560/59; 568/743

[58] Field of Search ........... 260/465 F, 619 D, 613 R, 260/473 S, 520 R, 559 R; 560/59

[56] References Cited

U.S. PATENT DOCUMENTS

| | | | |
|---|---|---|---|
| 2,304,669 | 12/1942 | Adams | 260/619 |
| 3,859,306 | 1/1975 | Freedman | 260/619 D X |

*Primary Examiner*—Dolph H. Torrence
*Attorney, Agent, or Firm*—Charles W. Ashbrook; Everet F. Smith

[57] ABSTRACT

Novel 1-hydroxy-3-alkyl-6,7,8,9,10,11-hexahydrodibenz[b,d]oxepins are prepared from cyclohexenyl resorcinol derivatives and are useful as central nervous system depressants.

5 Claims, No Drawings

CYCLOHEXENYL RESORCINOL DERIVATIVES

This is a division of application Ser. No. 638,019 filed Dec. 5, 1975 and now abandoned.

BACKGROUND OF THE DISCLOSURE

Dibenzoxepins known to date generally are dibenz[b,f]oxepin derivatives. For example, Mastursi et al. described a number of dibenz[b,f]oxepinyl piperazine derivatives, some having analgesic activity; see U.S. Pat. No. 3,600,391. The compounds of this invention are hexahydrodibenz[b,d]oxepins, hitherto unknown. Such compounds are related to the dibenzo[b,d]pyran class of compounds, however, no method has heretofore been available for preparing the compounds of this invention.

SUMMARY OF THE INVENTION

This invention provides novel diben[b,d]oxepin derivatives. More particularly, the compounds of this invention are hexahydro-dibenz[b,d]oxepins having the general formula

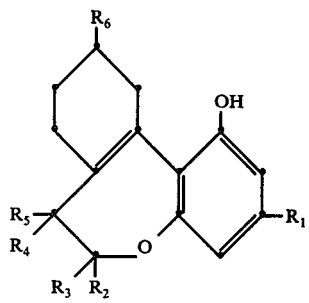

I in which $R_1$ is $C_5$–$C_{10}$ alkyl; $R_2$ and $R_3$ both are hydrogen or both are methyl, or taken together are oxo; $R_4$ and $R_5$ independently are hydrogen or methyl; and $R_6$ is $C_1$–$C_4$ alkyl, subject to the limitation that when $R_4$ and $R_5$ are hydrogen, $R_2$ and $R_3$ are other than methyl.

Additionally provided by this invention are compounds which are useful in the preparation of hexahydrodibenz[b,d]oxepins of the above formula. Such intermediate compounds provided by this invention are resorcinol derivatives having the formula

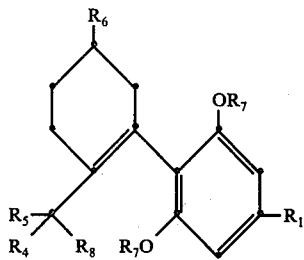

II in which $R_1$, $R_4$, $R_5$ and $R_6$ have the above-defined meanings; $R_7$ is hydrogen or benzyl; and $R_8$ is selected from the group consisting of chloro, bromo, cyano, chloromethyl, bromomethyl, $C_1$–$C_3$ alkoxycarbonyl, aminocarbonyl, hydroxycarbonyl, hydroxymethyl, aminomethyl and 2-hydroxyisopropyl; except that $R_8$ is other than aminocarbonyl when $R_4$ and $R_5$ both are other than methyl, and $R_8$ is other than chloro or bromo when either $R_4$ and $R_5$ are methyl.

DETAILED DESCRIPTION OF THE INVENTION

As used throughout this application and in the appended claims, the term "$C_5$–$C_{10}$ alkyl" refers to both straight and branched alkyl groups containing from 5 to 10 carbon atoms. Typical examples of such groups include n-pentyl, isopentyl, 1-methylpentyl, 1,1-dimethylpentyl, 1,2-dimethylpentyl, 1-ethylpentyl, n-hexyl, 1,2,3-trimethylhexyl, 2-ethylhexyl, n-heptyl, 1,1-dimethylheptyl, 1,2-dimethylheptyl, n-octyl, 1,2-dimethyloctyl, n-decyl, 3-ethyloctyl, isodecyl, and related groups.

The term $R_6$ refers to $C_1$–$C_4$ alkyl. Such groups include methyl, ethyl, n-propyl, isopropyl, n-butyl, isobutyl, and the like.

Examples of typical $C_1$–$C_3$ alkoxycarbonyl groups include methoxycarbonyl, ethoxycarbonyl and propoxycarbonyl.

The compounds of this invention can be readily prepared from tetrahydro-dibenzo[b,d]pyrans. More particularly, a 1-hydroxy-3-($C_5$–$C_{10}$-alkyl)-6-oxo-9-($C_1$–$C_4$ alkyl)-7,8,9,10-tetrahydro-6H-dibenzo[b,d]pyran is reduced to provide a resorcinol derivative, namely a 2-(2-hydroxymethyl-5-($C_1$–$C_4$-alkyl)-1-cyclohexenyl)-5-($C_5$–$C_{10}$ alkyl)resorcinol. Such resorcinol derivative is then converted by general methods to the resorcinol intermediates provided by this invention. Certain of the resorcinol intermediates provided herein can then be cyclized to provide a hexahydrodibenz[b,d]oxepin of formula I.

The synthesis of the compounds of this invention can be illustrated by the following general reaction scheme:

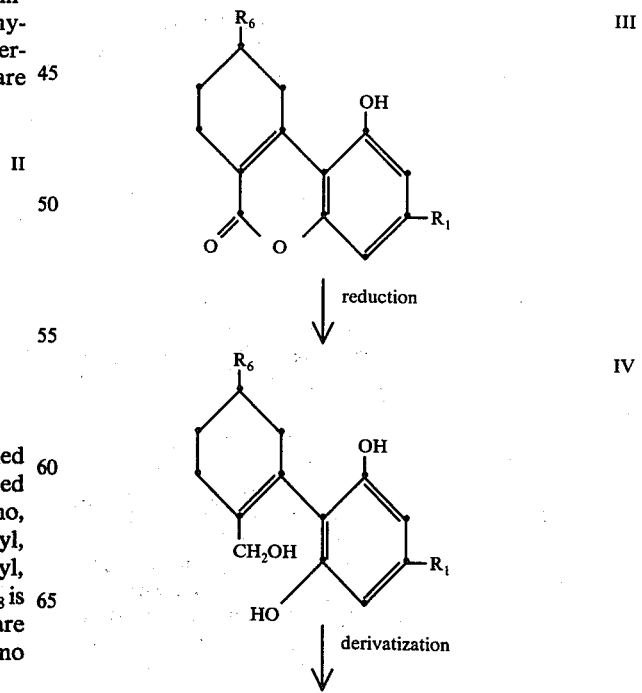

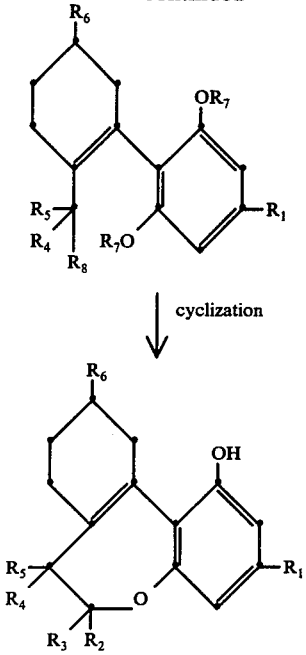

In accordance with this invention, a 1-hydroxy-3-($C_5$-$C_{10}$ alkyl)-6-oxo-9-($C_1$-$C_4$ alkyl)-7,8,9,10-tetrahydro-6H-dibenzo[b,d]pyran is reduced by reaction with a suitable reducing agent such as lithium aluminum hydride or sodium bis(2-methoxyethoxy)aluminum hydride to provide the corresponding 2-(2-hydroxymethyl-5-($C_1$-$C_4$ alkyl)-1-cyclohexenyl)-5-($C_5$-$C_{10}$ alkyl)-resorcinol, the compound of formula IV. Such conversion is well known in the art, and is more fully described by Loev et al. in *J. Med. Chem.*, 17, 1234 (1974). The tetrahydro-dibenzo[b,d]pyrans which are the starting materials for the above-mentioned reaction are readily available by routine methods and are known in the art; see for example, Adams et al. *J. Am. Chem. Soc.*, 70, 664 (1948). Typical examples of 2-(2-hydroxymethyl-5-($C_1$-$C_4$ alkyl)-1-cyclohexenyl)-5-($C_5$-$C_{10}$ alkyl)resorcinols prepared by hydrolysis of the corresponding tetrahydrodibenzo[b,d]pyran include:

2-(2-hydroxymethyl-5-methyl-1-cyclohexenyl)-5-n-hexyl-resorcinol;

2-(2-hydroxymethyl-5-ethyl-1-cyclohexenyl)-5-n-heptyl-resorcinol;

2-(2-hydroxymethyl-5-n-propyl-1-cyclohexenyl)-5-(1,2-dimethyloctyl)resorcinol;

2-(2-hydroxymethyl-5-isopropyl-1-cyclohexenyl)-5-(1,1-dimethylheptyl)resorcinol; and the like.

The resorcinol derivatives thus prepared are readily converted to the intermediate resorcinols of this invention by utilizing chemical principals known to those skilled in the art. For instance, the phenolic hydroxyl groups of a 2-(2-hydroxymethyl-5-($C_1$-$C_4$ alkyl)-1-cyclohexenyl)-5-($C_5$-$C_{10}$ alkyl)resorcinol can be protected with any of a number of normal phenolic hydroxyl protecting groups. Preferably, such resorcinol derivative is dibenzylated by reaction with benzyl chloride or benzyl bromide to provide the corresponding 2-(2-hydroxymethyl-5-($C_1$-$C_4$ alkyl)-1-cyclohexenyl)-5-($C_5$-$C_{10}$ alkyl)-dibenzylresorcinol. The dibenzylation reaction typically is carried out in an organic solvent such as ethyl alcohol, and preferably in the presence of a base such as potassium carbonate. The reaction is normally complete within 20 to 40 hours when carried out at about 50° to 100° C. The product can be isolated simply by removing the solvent, and further purification can be accomplished by solid-liquid chromatography over a solid support such as silica gel. Examples of compounds typically prepared include:

2-(2-hydroxymethyl-5-methyl-1-cyclohexenyl)-5-n-hexyl-dibenzylresorcinol; and 2-(2-hydroxymethyl-5-methyl-1-cyclohexenyl)-5-(1,2-dimethylheptyl)-dibenzylresorcinol.

The dibenzylresorcinol derivatives thus prepared are next reacted with a halogenating agent such as thionyl chloride or phosphorus tribromide to provide the corresponding 2-(2-halomethyl-5-($C_1$-$C_4$ alkyl)-1-cyclohexenyl)-5-($C_5$-$C_{10}$ alkyl)dibenzylresorcinol, in which the term "halo" refers to both chloro and bromo. Such compounds are represented by formula II when $R_7$ is benzyl and $R_8$ is halo. The halogenation reactions typically are carried out by mixing approximately equimolar qunatities of the appropriate 2-hydroxymethylcyclohexenyl-dibenzylresorcinol derivative and the halogenating agent in a solvent such as diethyl ether or dichloromethane. The reaction is best carried out at a temperature below about 50° C., normally at about 20° to 30° C. A base such as pyridine or triethylamine can be added to the reaction mixture if desired to act as an acid scavenger. When the reaction is complete, usually after about 1 to 2 hours, the solvent is simply removed by evaporation to provide the product. If desired, the 2-(2-halomethyl-5-($C_1$-$C_4$ alkyl)-1-cyclohexenyl)-5-($C_5$-$C_{10}$ alkyl)dibenzylresorcinol so formed can be further purified by chromatography. Examples of typical dibenzylresorcinol derivatives thus prepared and encompassed within this invention include:

2-(2-bromomethyl-5-methyl-1-cyclohexenyl)-5-n-pentyl-dibenzylresorcinol;

2-(2-chloromethyl-5-ethyl-1-cyclohexenyl)-5-n-octyl-dibenzylresorcinol;

2-(2-bromomethyl-5-n-propyl-1-cyclohexenyl)-5-(1,2-dimethylheptyl)-dibenzylresorcinol; and 2-(2-chloromethyl-5-n-butyl-1-cyclohexenyl)-5-(2-methylnonyl)-dibenzylresorcinol.

The 2-(2-halomethyl-5-($C_1$-$C_4$ alkyl)-1-cyclohexenyl)-5-($C_5$-$C_{10}$ alkyl)-dibenzylresorcinols thus formed are next reacted with sodium cyanide or potassium cyanide to effect a displacement of the halo atom by cyanide anion, thus providing the corresponding 2-(2-cyanomethyl-5-($C_1$-$C_4$ alkyl)-1-cyclohexenyl)-5-($C_5$-$C_{10}$alkyl) dibenzylresorcinols. Such compounds are represented by formula II when $R_7$ is benzyl and $R_8$ is cyano. The halomethyl derivative and sodium or potassium cyanide generally are utilized in approximately equimolar amounts. The reactants preferably are combined in a polar solvent such as dimethyl sulfoxide or dimethylformamide, and when the reaction is carried out at about 25° C., it is substantially complete within 10 to 20 hours. Isolation of the product is accomplished by adding water to the reaction mixture, and extraction of the product therefrom into a suitable water immiscible solvent such as diethyl ether, ethyl acetate, or chloroform. Removal of the solvent from the extracts provides the product, a 2-(2-cyanomethyl-5-($C_1$-$C_4$ alkyl)-1-cyclohexenyl)-5-($C_5$-$C_{10}$ alkyl)dibenzylresorcinol. Such compound often exists as an oil and can be further purified if desired by routine methods such as column chromatography and high pressure liquid chromatography. Typical examples of such 2-(2-cyanomethyl-5-

($C_1$-$C_4$ alkyl)-1-cyclohexenyl)-5-($C_5$-$C_{10}$ alkyl)dibenzylresorcinols so prepared include:

2-(2-cyanomethyl-5-methyl-1-cyclohexenyl)-5-(1,2-dimethylheptyl)-dibenzylresorcinol;

2-(2-cyanomethyl-5-ethyl-1-cyclohexenyl)-5-(n-decyl)-dibenzylresorcinol;

2-(2-cyanomethyl-5-isopropyl-1-cyclohexenyl)-5-isohexyl-dibenzylresorcinol; and 2-(2-cyanomethyl-5-n-butyl-1-cyclohexenyl)-5-(1,1-dimethylheptyl)-dibenzylresorcinol.

Such 2-(2-cyanomethyl-5-($C_1$-$C_4$ alkyl)-1-cyclohexenyl)-5-($C_5$-$C_{10}$ alkyl)dibenzylresorcinols are key intermediates in the preparation of the dibenzoxepins of this invention. Such dibenzylresorcinol derivatives can be mono-methylated and dimethylated to provide 2-[2-(1-cyanoethyl)-5-($C_1$-$C_4$ alkyl)-1-cyclohexenyl]-5-($C_5$-$C_{10}$ alkyl)dibenzylresorcinols and 2-[2-(1-cyano-1-methylethyl)-5-($C_1$-$C_4$ alkyl)-1-cyclohexenyl]-5-($C_5$-$C_{10}$ alkyl)-dibenzylresorcinols respectively, compounds of formula II when one or both of $R_4$ and $R_5$ are methyl. The 2-(2-cyanomethyl-5-($C_1$-$C_4$ alkyl)-1-cyclohexenyl)-5-($C_5$-$C_{10}$ alkyl)dibenzylresorcinols can be solvolyzed to the corresponding 2-(2-hydroxycarbonylmethyl) or 2-[2-($C_1$-$C_3$ alkoxycarbonylmethyl)-5-($C_1$-$C_4$ alkyl)-1-cyclohexenyl]-5-($C_5$-$C_{10}$ alkyl)dibenzylresorcinols, compounds of formula II when $R_8$ is hydroxycarbonyl or $C_1$-$C_3$ alkoxycarbonyl. Still further, such 2-(2-cyanomethyl-5-($C_1$-$C_4$ alkyl)-1-cyclohexenyl)-5-($C_5$-$C_{10}$ alkyl)dibenzylresorcinols can be directly cyclized with simultaneous removal of the benzyl protecting groups to provide a hexahydro-dibenz[b,d]oxepin of this invention.

More particularly, a 2-(2-cyanomethyl-5-($C_1$-$C_4$ alkyl)-1-cyclohexenyl)-5-($C_5$-$C_{10}$ alkyl)dibenzylresorcinol can be mono-methylated and di-methylated by reaction with a methylating agent such as methyl iodide in the presence of a suitable base. Mono-methylation is accomplished by carrying out the reaction in the presence of a base such as potassium tert-butoxide, while di-methylation is accomplished by carrying out the reaction in the presence of a stronger base such as lithium diisopropylamide. For example, reaction of a dibenzylresorcinol such as 2-(2-cyanomethyl-5-ethyl-1-cyclohexenyl)-5-(1,2-dimethylheptyl)dibenzylresorcinol with about a 2 to 10 molar excess of methyl iodide in the presence of potassium tert-butoxide affords 2-[2-(1-cyanoethyl)-5-ethyl-1-cyclohexenyl]-5-(1,2-dimethylheptyl)dibenzylresorcinol. Alternatively, reaction of the above-named dibenzylresorcinol with a 2 to 10 molar excess of methyl iodide in the presence of lithium diisopropylamide effects dimethylation to provide 2-[2-(1-cyano-1-methylethyl)-5-ethyl-1-cyclohexenyl]-5-(1,2-dimethylheptyl)dibenzylresorcinol. Such methylation reactions typically are carried out in an organic solvent such as benzene, diethyl ether, toluene, dimethyl sulfoxide, dioxane, and the like. The reaction normally is complete within about 5 to 20 hours when carried out at a temperature ranging from about 0° to 60° C. The product is isolated by simply removing any reaction solvent, and further purification can be accomplished if desired by column chromatography, crystallization, or the like.

Aqueous alkaline hydrolysis of either a 2-(2-cyanomethyl-5-($C_1$-$C_4$ alkyl)-1-cyclohexenyl)-5-($C_5$-$C_{10}$ alkyl)-dibenzylresorcinol or a 2-[2-(1-cyanoethyl)-5-($C_1$-$C_4$ alkyl)-1-cyclohexenyl]-5-($C_5$-$C_{10}$ alkyl)-dibenzylresorcinol converts the cyano group to a hydroxycarbonyl group, thus providing a 2-(2-hydroxycarbonylmethyl-5-($C_1$-$C_4$ alkyl)-1-cyclohexenyl)-5-($C_5$-$C_{10}$ alkyl)dibenzylresorcinol or a 2-[2-(1-hydroxycarbonylethyl)-5-($C_1$-$C_4$ alkyl)-1-cyclohexenyl]-5-($C_5$-$C_{10}$ alkyl)dibenzylresorcinol respectively. In contrast, aqueous alkaline hydrolysis of a 2-[2-(1-cyano-1-methyl-ethyl)-5-($C_1$-$C_4$ alkyl)-1-cyclohexenyl]-5-($C_5$-$C_{10}$ alkyl)-dibenzylresorcinol effects only partial hydrolysis of the cyano group to provide an amide, namely a 2-[2-(1-amino-carbonyl-1-methylethyl)-5-($C_1$-$C_4$ alkyl)-1-cyclohexenyl]-5-($C_5$-$C_{10}$ alkyl)dibenzylresorcinol, the compound of formula II wherein $R_7$ is benzyl and $R_8$ is aminocarbonyl. Such aqueous alkaline hydrolysis reactions typically are accomplished by simply reacting the cyano derivative with an aqueous base such as aqueous sodium hydroxide or potassium hydroxide. Organic solvents such as ethanol and dioxane can be utilized as reaction solvents if desired. The hydrolysis of the cyano group typically is complete after about 10 to 40 hours when carried out at a temperature of about 30° to 100° C. Isolation of the hydrolyzed product can be accomplished by normal extraction procedures, and the product can be further purified if desired by general methods such as chromatography. Examples of hydrolyzed products so formed include:

2-(2-hydroxycarbonylmethyl-5-ethyl-1-cyclohexenyl)-5-(1,2-dimethylpentyl)dibenzylresorcinol;

2-[2-(1-hydroxycarbonylethyl)-5-methyl-1-cyclohexenyl]-5-(1,1-dimethylheptyl)dibenzylresorcinol; and 2-[2-(1-aminocarbonyl-1-methylethyl)-5-n-butyl-1-cyclohexenyl]-5-(1-ethylpentyl)dibenzylresorcinol;

In addition to the aforementioned aqueous alkaline hydrolysis of the cyano group of a 2-(2-cyanomethyl-5-($C_1$-$C_4$ alkyl)-1-cyclohexenyl)-5-($C_5$-$C_{10}$ alkyl)dibenzylresorcinol, such cyano group can be converted to a $C_1$-$C_3$ alkoxycarbonyl moiety by alcoholysis with a $C_1$-$C_3$ alcohol in the presence of an acid such as hydrochloric acid. More particularly, reaction of such cyano compound with an alcohol such as methanol, ethanol, propanol, or isopropanol, in the presence of an acid, effects alcoholysis to provide the corresponding ester, a 2-[2-($C_1$-$C_3$-alkoxycarbonylmethyl)-5-($C_1$-$C_4$ alkyl)-1-cyclohexenyl]-5-($C_5$-$C_{10}$ alkyl)dibenzylresorcinol. Such alcoholysis reactions are quite general and are readily accomplished by dissolving the cyano compound in an alcohol, and heating the solution in the presence of an acid, preferably gaseous hydrochloric acid, to a temperature ranging from about 30° to 150° C., generally for about 10 to 30 hours. The product is an ester and is isolated by removal of the reaction solvent, followed by normal purification if desired.

The 2-[2-(1-aminocarbonyl-1-methylethyl)-5-($C_1$-$C_4$ alkyl)-1-cyclohexenyl]-5-($C_5$-$C_{10}$ alkyl)dibenzylresorcinol prepared by aqueous alkaline hydrolysis as mentioned hereinabove can also be converted to a 2-[2-(1-($C_1$-$C_3$ alkoxycarbonyl)-1-methylethyl)-5-($C_1$-$C_4$ alkyl)-1-cyclohexenyl]-5-($C_5$-$C_{10}$ alkyl)dibenzylresorcinol by alcoholysis in the presence of an acid. Such reaction is carried out as the aforementioned alcoholysis of a cyano compound. For example, reaction of 2-[2-(1-aminocarbonyl-1-methylethyl)-5-methyl-1-cyclohexenyl]-5-n-heptyl-dibenzyl-resorcinol with ethanol in the presence of gaseous hydrobromic acid effects alcoholysis of the amido group to provide an ester, for example 2-[2-(1-ethoxycarbonyl-1-methylethyl)-5-methyl-1-cyclohexenyl]-5-n-heptyl-dibenzylresorcinol.

It will be recognized that the dibenzylresorcinol derivatives hereinabove referred to can be debenzylated whenever desired by normal procedures such as hydrogenation. More particularly, a dibenzylresorcinol can be treated with hydrogen gas in the presence of a catalyst such as palladium on carbon, thus removing the benzyl protecting groups and regenerating the unprotected resorcinol derivative. For example, a dibenzylresorcinol such as 2-(2-hydroxycarbonyl-methyl-5-ethyl-1-cyclohexenyl)-5-n-pentyldibenzylresorcinol can be hydrogenated in the presence of palladium on charcoal in a suitable solvent such as ethanol to provide the corresponding unprotected resorcinol, namely 2-(2-hydroxycarbonylmethyl-5-ethyl-1-cyclohexenyl)-5-n-pentylresorcinol. Typical examples of such resorcinol derivatives include:

2-(2-hydroxycarbonylmethyl-5-methyl-1-cyclohexenyl)-5-(1,2-dimethylheptyl)resorcinol;
2-[2-(1-hydroxycarbonylethyl)-5-methyl-1-cyclohexenyl]-5-(1,2,3-trimethylheptyl)resorcinol;
2-[2-(1-hydroxycarbonylethyl)-5-n-propyl-1-cyclohexenyl]-5-(1-ethylpentyl)resorcinol;
2-[2-(1-ethoxycarbonyl-1-methylethyl)-5-methyl-1-cyclohexenyl]-5-n-hexylresorcinol;
2-[2-(1-aminocarbonyl-1-methylethyl)-5-ethyl-1-cyclohexenyl]-5-n-pentylresorcinol;

Certain of the aforementioned unprotected resorcinol derivatives can next be cyclized to provide certain of the hexahydro-dibenz[b,d]oxepins of this invention. In particular, those resorcinol derivatives having the formula

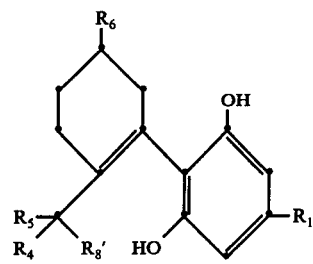

in which $R_8'$ is hydroxycarbonyl or aminocarbonyl can be cyclized to provide 6-oxo-hexahydro-dibenz[b,d]oxepins. Such cyclization reactions can better be understood by observing the following sequence:

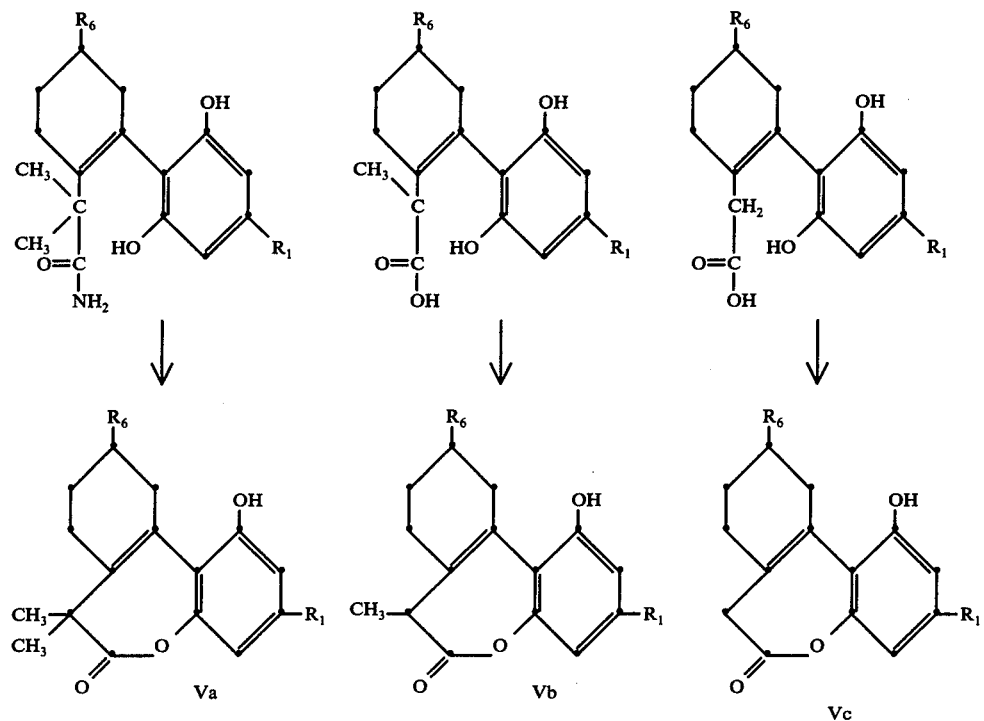

The cyclization of a 2-[2-(1-aminocarbonyl-1-methylethyl)-5-($C_1$–$C_4$ alkyl)-1-cyclohexenyl]-5-($C_5$–$C_{10}$ alkyl)resorcinol can be effected by simply heating such compound to a temperature of about 200° to 300° C. The reaction generally is carried out in the absence of solvent, and normally is complete within 5 to 30 minutes. The product can be purified by chromatography if desired. The hexahydro-dibenz[b,d]oxepin so obtained is a 1-hydroxy-3-($C_5$–$C_{10}$ alkyl)-6-oxo-7,7-dimethyl-10-($C_1$–$C_4$ alkyl)-6,7,8,9,10,11-hexahydro-dibenz[b,d]oxepin, (Va).

The cyclization of a 2-(2-hydroxycarbonylmethyl-5-($C_1$–$C_4$ alkyl)-1-cyclohexenyl)-5-($C_5$–$C_{10}$ alkyl)resorcinol or a 2-[2-(1-hydroxycarbonylethyl)-5-($C_1$–$C_4$ alkyl)-1-cyclohexenyl]-5-($C_5$–$C_{10}$ alkyl)resorcinol can be effected by reaction with any of a number of dehydrating agents, such as those commonly utilized in peptide synthesis. Such commonly used dehydrating agents include carbodiimides such as N,N'-dicyclohexycarbodiimide and N,N'-diisopropylcarbodiimide. Such cyclization reactions typically are carried out in an organic solvent such as dichloromethane, benzene, acetonitrile, or the like. The cyclization normally is complete within about ½ to 5 hours when carried out at about 20° to 30° C. The product, a 6-oxo-dibenz[b,d]oxepin derivative, is readily isolated by removal of any reaction solvents, and if desired the product can be further purified by standard procedures such as chromatography or crystallization. As a typical example of such cyclization reaction, a resorcinol such as 2-[2-(1-hydroxycarbonylethyl)-5-n-propyl-1-cyclohexenyl]-5-(1,2-dimethyloctyl)resorcinol can be reacted with approximately an equimolar quantity of N,N'-dicyclohexylcarbodiimide in a solvent such as dichloromethane. The reaction mixture is stirred for about 2 hours at 25° C. to provide 1-hydroxy-3-(1,2-dimethyloctyl)-6-oxo-7-methyl-10-n-propyl-6,7,8,9,10,11-hexahydro-dibenz[b,d]oxepin. Additional examples of routinely prepared 6-oxo-hexahydrodibenz[b,d]oxepins of this invention include:

1-hydroxy-3-(1-ethylbutyl)-6-oxo-7,7,10-trimethyl-6,7,8,9,10,11-hexahydro-dibenz[b,d]oxepin;
1-hydroxy-3-n-heptyl-6-oxo-10-ethyl-6,7,8,9,10,11-hexahydro-dibenz[b,d]oxepin;
1-hydroxy-3-isodecyl-6-oxo-7-methyl-10-isobutyl-6,7,8,9,10,11-hexahydro-dibenz[b,d]oxepin;
1-hydroxy-3-(1,1-dimethylheptyl)-6-oxo-7,7-dimethyl-10-n-butyl-6,7,8,9,10,11-hexahydro-dibenz[b,d]oxepin; and
1-hydroxy-3-n-nonyl-6-oxo-7,10-dimethyl-6,7,8,9,10,11-hexahydro-dibenz[b,d]oxepin.

Alcoholysis of either a 2-[2-(1-aminocarbonyl-1-methylethyl)-5-($C_1$-$C_4$ alkyl)-1-cyclohexenyl]-5-($C_5$-$C_{10}$ alkyl)resorcinol, a 2-[2-(1-cyanoethyl)-5-($C_1$-$C_4$ alkyl)-1-cyclohexenyl]-5-($C_5$-$C_{10}$ alkyl)resorcinol, or a 2-(2-cyanomethyl-5-($C_1$-$C_4$ alkyl)-1-cyclohexenyl]-5-($C_5$-$C_{10}$ alkyl)resorcinol, provides the corresponding $C_1$-$C_3$ alkoxycarbonyl derivative. Such alkoxycarbonyl derivatives are valuable intermediates in the preparation of a number of novel dibenz[b,d]oxepins of this invention. For example, the alkoxycarbonyl derivatives of unprotected resorcinols, that is compounds having the general formula

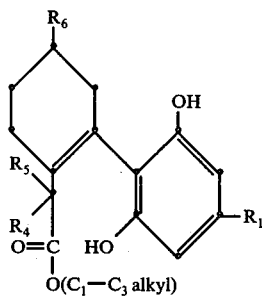

VI can be reduced to the corresponding 2-(2-hydroxyethyl-5-($C_1$-$C_4$ alkyl)-1-cyclohexenyl)-5-($C_5$-$C_{10}$ alkyl)resorcinol, or alternatively such ester compounds can be hydrolyzed to provide an acid, and still further such esters can be reacted with methyl Grignard reagent to provide the corresponding tertiary alcohol, namely a 2-[2-(2-hydroxyisopropylmethyl)-5-($C_1$-$C_4$ alkyl)-1-cyclohexenyl]-5-($C_5$-$C_{10}$ alkyl)resorcinol.

More particularly, reduction of a 2-[2-($C_1$-$C_3$ alkoxycarbonylmethyl)-5-($C_1$-$C_4$ alkyl)-1-cyclohexenyl]-5-($C_5$-$C_{10}$ alkyl)resorcinol provides the corresponding 2-hydroxyethyl derivative having the general formula

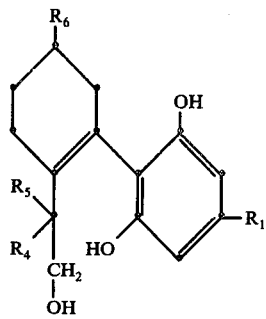

VII

The reduction of such alkoxycarbonyl derivatives can be accomplished by reaction with any of a number of reducing agents, including hydride reducing agents such as lithium aluminum hydride and lithium aluminum tri-tert.-butoxy hydride. The reduction reaction generally is carried out by stirring the alkoxycarbonyl derivative with an excess of the reducing agent in a suitable solvent such as diethyl ether, dioxane, or benzene. The reaction normally is carried out at about 0° to 50° C., and usually is substantially complete within 1 to 5 hours. The product is then easily isolated by decomposing any remaining reducing agent, for instance by the addition of an acid such as aqueous hydrochloric acid, and then removal of any reaction solvent. The product, a 2-[2-(2-hydroxyethyl)-5-($C_1$-$C_4$ alkyl)-1-cyclohexenyl]-5-($C_5$-$C_{10}$ alkyl)resorcinol having the above formula, can be further purified if desired by crystallization or chromatography. Examples of such hydroxyethyl derivatives prepared according to the above-described reduction process include:

2-[2-(1-hydroxymethyl-1-methylethyl)-5-methyl-1-cyclohexenyl]-5-n-pentylresorcinol;
2-[2-(1-hydroxymethyl-1-methylethyl)-5-n-propyl-1-cyclohexenyl]-5-(1,2-dimethylhexyl)resorcinol;
2-[2-(1-hydroxymethylethyl)-5-methyl-1-cyclohexenyl]-5-(1-n-propylheptyl)resorcinol;
2-[2-(1-hydroxymethylethyl)-5-ethyl-1-cyclohexenyl]-5-n-decylresorcinol;
2-[2-(2-hydroxyethyl)-5-methyl-1-cyclohexenyl]-5-(1,1-dimethylheptyl)resorcinol; and
2-[2-(2-hydroxyethyl)-5-n-butyl-1-cyclohexenyl]-5-(1,2,3-trimethylheptyl)resorcinol.

The hydroxyethyl derivatives so prepared are valuable intermediates since they can be conveniently dehydrated to provide a hexahydro-dibenz[b,d]oxepin, a compound of formula I when $R_2$ and $R_3$ are hydrogen. Such compounds are represented by the general structural formula

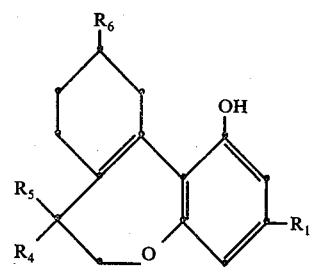

VIII

Such dehydration reaction of the aforementioned hydroxyethyl resorcinol derivative to provide the hexahydro-dibenz[b,d]-oxepin of the above formula can be accomplished by any of a number of methods, and will be described in detail hereinbelow.

As has already been indicated, a 2-[2-($C_1$–$C_3$ alkoxycarbonylmethyl)-5-($C_1$–$C_4$ alkyl)-1-cyclohexenyl]-5-($C_5$–$C_{10}$ alkyl)resorcinol can be reacted with a methyl Grignard reagent to effect a normal reductive alkylation of the ester group so as to provide a tertiary alcohol, namely a 2-[2-(2-hydroxyisopropylmethyl)-5-($C_1$–$C_4$ alkyl)-1-cyclohexenyl]-5-($C_5$–$C_{10}$ alkyl)resorcinol of the general formula

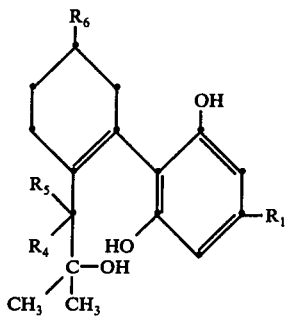

IX

The reaction of methyl Grignard reagent with the aforementioned ester is carried under normal Grignard reaction conditions of solvent, temperature, and the like. For instance, a $C_1$–$C_3$ alkoxycarbonylmethyl resorcinol derivative such as 2-[2-(1-methoxycarbonyl-1-methylethyl)-5-methyl-1-cyclohexenyl]-5-(1,2-dimethylpentyl)resorcinol can be reacted with about a 3 to 5 molar excess of methyl magnesium bromide in a solvent such as benzene or diethyl ether to provide, after hydrolysis, the corresponding tertiary alcohol, namely 2-[2-(1-(2-hydroxyisopropyl)-1-methylethyl)-5-methyl-1-cyclohexenyl]-5-(1,2-dimethylpentyl)resorcinol. Such Grignard reaction typically is conducted at a temperature ranging from about 0° to 100° C., and usually is complete within about 2 to 20 hours. The tertiary alcohol which is formed is easily isolated by acidifying the reaction mixture, for instance by adding an aqueous mineral acid, and extracting the product into a suitable water-immiscible solvent such as diethyl ether or benzene. The product, a tertiary alcohol having the above formula, can be further purified if desired by standard procedures such as chromatography. Examples of tertiary alcohols so formed include:

2-[2-(2-hydroxyisopropylmethyl)-5-ethyl-1-cyclohexenyl]-5-n-pentylresorcinol;

2-[2-(1-(2-hydroxyisopropyl)ethyl)-5-n-propyl-1-cyclohexenyl]-5-n-octylresorcinol; and 2-[2-(1-(2-hydroxyisopropyl)-1-methylethyl)-5-n-butyl-1-cyclohexenyl]-5-(1-methylhexyl)resorcinol.

As hereinabove indicated, a 2-[2-(2-hydroxyethyl)-5-($C_1$–$C_4$ alkyl)-1-cyclohexenyl]-5-($C_5$–$C_{10}$ alkyl)resorcinol is readily dehydrated to provide a hexahydro-dibenz[b,d]-oxepin of this invention. The aforementioned hydroxyisopropyl tertiary alcohol prepared by reaction of methyl Grignard reagent with an ester is in fact a 2-[2-(2-hydroxyethyl)-5-($C_1$–$C_4$ alkyl)-1-cyclohexenyl]-5-($C_5$–$C_{10}$ alkyl)resorcinol, and accordingly can be dehydrated to provide a hexahydro-dibenz[b,d]oxepin of this invention. Such dehydration reactions can be accomplished by reacting the alcohol derivative with a suitable dehydrating agent, or alternatively by converting the alcohol derivative to a compound which will undergo cyclization under the influence of a basic catalyst. More particularly, a 2-[2-(2-hydroxyethyl)-5-($C_1$–$C_4$ alkyl)-1-cyclohexenyl]-5-($C_5$–$C_{10}$ alkyl)resorcinal having the general formula

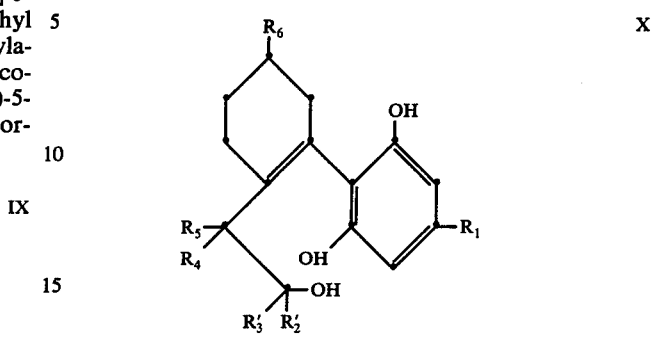

X in which $R_2'$ and $R_3'$ both are hydrogen or both are methyl, can be cyclized to the corresponding hexahydro-dibenz[b,d]oxepin by reaction with a dehydrating agent such as N,N'-dicyclohexylcarbodiimide, N,N'-diisopropylcarbodiimide, or a mineral acid. Such reaction typically is carried out by reacting approximately equimolar quantities of the alcohol having the above formula with a dehydrating agent, either in the absence of a reaction solvent, or if preferred, in a solvent such as dichloromethane or chloroform. The cyclization reaction generally is complete within about ½ to 5 hours when carried out at a temperature ranging from about 20° to 200° C. The product, a hexahydro-dibenz[b,d]oxepin, can be readily isolated by filtration or by chromatography.

The alcohols having the above formula can alternatively be converted to a reactive derivative which will then cyclize to a dibenz[b,d]oxepin when treated with a basic catalyst. More particularly, a 2-[2-(2-hydroxyethyl)-5-($C_1$–$C_4$ alkyl)-1-cyclohexenyl]-5-($C_5$–$C_{10}$ alkyl)-resorcinol can be treated with a halogenating agent such as phosphorous tribromide or phosphorous trichloride in order to convert the hydroxyethyl moiety to the corresponding bromoethyl or chloroethyl derivative, the compound of formula II wherein $R_7$ is hydrogen and $R_8$ is bromomethyl or chloromethyl. For example, reaction of an alcohol such as 2-[2-(2-hydroxyethyl)-5-methyl-1-cyclohexenyl]-5-n-pentylresorcinol with phosphorous tribromide effects bromination to afford the corresponding bromoethyl derivative, namely 2-[2-(2-bromoethyl)-5-methyl-1-cyclohexenyl]-5-n-pentylresorcinol. The haloethyl derivative so formed is next cyclized by reaction with a base such as sodium carbonate, potassium carbonate, or the like. For example, reaction of 2-[2-(2-bromoethyl)-5-methyl-1-cyclohexenyl]-5-n-pentylresorcinol with about a 2 to 6 molar excess of potassium carbonate in a solvent such as methyl ethyl ketone effects cyclization to provide 1-hydroxy-3-n-pentyl-10-methyl-6,7,8,9,10,11-hexahydro-dibenz[b,d]oxepin.

The 2-[2-(2-hydroxyethyl)-5-($C_1$–$C_4$ alkyl)-1-cyclohexenyl]-5-($C_5$–$C_{10}$ alkyl)resorcinol having the above formula (X) can additionally be cyclized to the corresponding dibenz[b,d]oxepin derivative by reaction with an acid such as gaseous hydrogen bromide or gaseous hydrogen chloride, thus alleviating the need for intermediate conversion to a haloethyl derivative. Such cyclization generally is carried out in an organic solvent such as methanol, ethanol, diethyl ether, or the like, and at a temperature of about 20° to 30° C. For instance, a 2-hydroxyethyl derivative such as 2-[2-(1-(2-hydroxyisopropyl)-1-methylethyl)-5-ethyl-1-cyclohexenyl]-5-n-heptylresorcinol can be stirred with excess hydrogen chloride in a solvent such as diethyl ether, thus effecting cyclization to afford 1-hydroxy-3-n-heptyl-6,6,7,7-tetramethyl-10-ethyl-6,7,8,9,10,11-hexahydro-dibenz[b,d]oxepin. Such compound normally is isolated by simply removing the reaction solvent, for instance by evaporation.

Examples of hexahydro-dibenz[b,d]oxepins routinely prepared from 2-[2-(2-hydroxyethyl)-5-($C_1$-$C_4$ alkyl)-1-cyclohexenyl]-5-($C_5$-$C_{10}$ alkyl)resorcinols according to the above-described cyclization processes include:

1-hydroxy-3-n-nonyl-10-methyl-6,7,8,9,10,11-hexahydro-dibenz[b,d]oxepin;
1-hydroxy-3-(1-ethylpentyl)-10-isobutyl-6,7,8,9,10,11-hexahydro-dibenz[b,d]oxepin;
1-hydroxy-3-(1,2-dimethylheptyl)-7,10-dimethyl-6,7,8,9,10,11-hexahydro-dibenz[b,d]oxepin;
1-hydroxy-3-(1,1-dimethylhexyl)-7-methyl-10-ethyl-6,7,8,9,10,11-hexahydro-dibenz[b,d]oxepin;
1-hydroxy-3-isopentyl-6,6,7-trimethyl-10-n-propyl-6,7,8,9,10,11-hexahydro-dibenz[b,d]oxepin;
1-hydroxy-3-(1,2-dimethyloctyl)-6,6,7,10-tetramethyl-6,7,8,9,10,11-hexahydro-dibenz[b,d]oxepin;
1-hydroxy-3-(1,2,3-trimethyl)-7,7-dimethyl-10-ethyl-6,7,8,9,10,11-hexahydro-dibenz[b,d]oxepin;
1-hydroxy-3-n-heptyl-7,7,10-trimethyl-6,7,8,9,10,11-hexahydro-dibenz[b,d]oxepin;
1-hydroxy-3-(1,1-dimethylheptyl)-6,6,7,7-tetramethyl-10-n-butyl-6,7,8,9,10,11-hexahydro-dibenz[b,d]oxepin;
1-hydroxy-3-n-pentyl-6,6,7,7-tetramethyl-10-isopropyl-6,7,8,9,10,11-hexahydro-dibenz[b,d]oxepin;
1-hydroxy-3-n-hexyl-6,6,7,7-tetramethyl-10-tert-butyl-6,7,8,9,10,11-hexahydro-dibenz[b,d]oxepin.

The novel hexahydro-dibenz[b,d]oxepins of this invention are of particular importance due to their depressant effects upon the central nervous system when administered to mammals. Such compounds are thus useful as anti-anxiety and tranquilizer type drugs. Such hexahydro-dibenz[b,d]oxepins have demonstrated useful depressant activity when tested by normal and accepted screening procedures. For instance, the dibenzoxepin derivatives of this invention have demonstrated useful activity when tested in the standard septal-lesioned rat assay and the muricidal rat assay. For example, 1-hydroxy-3-(1,1-dimethylheptyl)-10-methyl-6,7,8,9,10,11-hexahydro-dibenz[b,d]oxepin demonstrated a response in both the septal-lesioned rat assay and the muricidal rat assay at a minimum effective dose of 1.25 mg/kg of body weight when administered orally. The novel dibenz[b,d]oxepin derivatives additionally demonstrated a depressant effect when administered to mice. For instance, 1-hydroxy-3-(1,1-dimethylheptyl)-6-oxo-10-methyl-6,7,8,9,10,11-hexahydroxy-dibenz[b,d]oxepin caused a CNS depressant effect when administered orally to mice at doses as low as 5 mg./kg. of body weight.

The hexahydro-dibenz[b,d]oxepins of this invention can accordingly be used as pharmaceutical agents, and can be administered to humans to cause a psycotropic effect. When thus used, the dibenzoxepin derivatives of this invention typically are formulated with conventional pharmaceutical diluents and carriers. Such formulation can take the form of tablets, capsules, powders, and the like, for convenient oral administration, or alternatively as syrups, solutions, suspensions, and the like, for convenient parenteral administration. Commonly used pharmaceutical diluents and carriers include starch, sucrose, cellulose derivatives, glycerine, mannitol, and the like.

The hexahydro-dibenz[b,d]oxepins of this invention normally will be administered to a subject in need of treatment as a pharmaceutical composition containing from about 0.1 to 50 percent by weight of at least one of such active compounds. Such compositions will be administered to a subject as needed, the exact dosage regimen to be determined as the individual situation requires.

In order to more fully understand certain aspects of this invention, the following detailed examples are presented. Such examples are, however, purely illustrative of general methods of preparation of dibenzoxepin derivatives and intermediates therefor, and should not be construed as limiting the invention to any particular aspect.

EXAMPLE 1

2-(2-Hydroxymethyl-5-methyl-1-cyclohexenyl)-5-n-pentyl-resorcinol

A solution of 90 ml. of a seventy percent solution of sodium bis(2-methoxyethoxy)aluminum hydride in 80 ml. of benzene was cooled in an ice-water bath and stirred while a suspension of 13.0 g. of 1-hydroxy-3-n-pentyl-6-oxo-9-methyl-7,8,9,10-tetrahydro-6H-dibenzo[b,d]pyran in 220 ml. of benzene was added portionwise over 15 minutes. The reaction mixture was warmed to about 25° C. and stirred for 2 hours. The reaction mixture was again cooled in an ice-water bath and stirred while 800 ml. of 10 percent aqueous hydrochloric acid solution was added. The aqueous acidic reaction mixture was extracted several times with diethyl ether. The ethereal extracts were combined, washed with water, and dried. Removal of the solvent under reduced pressure provided 2-(2-hydroxymethyl-5-methyl-1-cyclohexenyl)-5-n-pentyl-resorcinol as a white crystalline solid. M.P. 109°–11° C.

Analysis Calc. for $C_{19}H_{28}O_3$ Theory: C, 74.96; H, 9.27. Found: C, 74.75; H, 9.36.

EXAMPLE 2

2-(2-Hydroxymethyl-5-methyl-1-cyclohexenyl)-5-n-pentyldibenzylresorcinol

A solution of 13.2 g. of 2-(2-hydroxymethyl-5-methyl-1-cyclohexenyl)-5-n-pentyl-resorcinol in 100 ml. of ethyl alcohol containing 11.5 g. of benzyl chloride and 6.6 g. of potassium carbonate was heated at reflux and stirred for 24 hours. The reaction mixture was cooled to room temperature and poured into 200 ml. of water. The aqueous reaction mixture was extracted several times with diethyl ether, and the ethereal extracts were combined, washed with water, and dried. Removal of the solvent under reduced pressure provided 15 g. of the product as a viscous oil. The oil was then dissolved in 20 ml. of benzene and chromatographed over 300 g. of silica gel, eluting with benzene and ethyl acetate. Fractions containing the product were combined and concentrated under reduced pressure to afford 10 48 g. of 2-(2-hydroxymethyl-5-methyl-1-cyclohexenyl)-5-n-pentyl-dibenzylresorcinol. M+ 484.

Analysis Calc. for $C_{33}H_{40}O_3$ Theory: C, 81.78; H, 8.32. Found: C, 82.06; H, 8.50.

nmr (CDCl$_3$): δ 5.1, (s, 4H, benzyl methylenes) δ 7.4, (s, 10H, benzyl aromatic)

EXAMPLE 3

2-(2-Chloromethyl-5-methyl-1-cyclohexenyl)-5-n-pentyldibenzylresorcinol

A solution of 4.85 g. of 2-(2-hydroxymethyl-5-methyl-1-cyclohexenyl)-5-n-pentyl-dibenzylresorcinol in 20 ml. of diethyl ether containing 0.1 ml. of pyridine was stirred at 25° C. while 2.55 g. of thionyl chloride was added in one portion. The reaction mixture was stirred for 1½ hours, and was then washed with water and dried. Removal of the solvent under reduced pressure provided 4.86 g. of the product as an orange liquid. The product so formed was chromatographed over 150 g. of silica gel, eluting with benzene. Evaporation of the solvent from the combined fractions provided 4.10 g. of 2-(2-chloromethyl-5-methyl-1-cyclohexenyl)-5-n-pentyl-dibenzylresorcinol. M+ 502 and 504.

Analysis Calc. for $C_{33}H_{39}O_2Cl$ Theory: C, 78.78; H, 7.81; Cl, 7.05. Found: C, 80.46; H, 8.06; Cl, 5.15.

EXAMPLE 4

2-(2-Bromomethyl-5-methyl-1-cyclohexenyl)-5-n-pentyldibenzylresorcinol

A solution of 7.62 g. of 2-(2-hydroxymethyl-5-methyl-1-cyclohexenyl)-5-n-pentyl-dibenzylresorcinol in 15 ml. of diethyl ether was stirred and cooled in an ice-water bath while 5.10 g. of phosphorus tribromide was added dropwise over 10 minutes. After the addition was complete, the reaction mixture was heated at reflux for 1 hour. The reaction mixture was poured into 50 g. of ice, and the resulting aqueous solution was extracted with diethyl ether. The ethereal extracts were separated, combined, washed with water, and dried. Removal of the solvent by evaporation under reduced pressure provided 7.82 g. of 2-(2-bromomethyl-5-methyl-1-cyclohexenyl)-5-n-pentyl-dibenzylresorcinol as a viscous oil.

nrm ($CDCl_3$): δ 5.04, (s, 4H, benzyl methylenes) δ 6.42, (s, 2H, resorcinol aromatic) δ 7.38, (s, 10H, benzyl aromatic)

EXAMPLE 5

2-(2-Cyanomethyl-5-methyl-1-cyclohexenyl)-5-n-pentyldibenzylresorcinol

A solution of 2.33 g. of 2-(2-bromomethyl-5-methyl-1-cyclohexenyl)-5-n-pentyl-dibenzylresorcinol in 10 ml. of dimethyl sulfoxide containing 416 mg. of sodium cyanide was stirred at about 25° C. for 12 hours. The reaction mixture was added to 100 ml. of water, and the aqueous solution was then extracted several times with diethyl ether. The ethereal extracts were combined, washed with 1N hydrochloric acid solution and with water, and dried. Removal of the solvent under reduced pressure afforded 2.01 g. of the product as an oil. The oil was chromatographed over 50 g. of silica gel, eluting with benzene. The fractions were combined and concentrated under reduced pressure to afford 1.67 g. of 2-(2-cyanomethyl-5-methyl-1-cyclohexenyl)-5-n-pentyl-dibenzylresorcinol as a colorless oil. M+ 493.

Analysis Calc. for $C_{34}H_{39}NO_2$ Theory: C, 82.72; H, 7.96; N, 2.84. Found: C, 82.57; H, 7.72; N, 2.71.

nmr ($CDCl_3$): δ 5.15, (s, 4H, benzyl methylenes) δ 7.45, (s, 10H, benzyl aromatics)

EXAMPLE 6

2-(2-Cyanomethyl-5-methyl-1-cyclohexenyl)-5-n-pentylresorcinol

A solution of 2.0 g. of 2-(2-cyanomethyl-5-methyl-1-cyclohexenyl)-5-n-pentyl-dibenzylresorcinol in 20 ml. of dichloromethane was cooled in an ice-water bath and stirred while a solution of 2.0 ml. of boron tribromide in 20 ml. of dichloromethane was added dropwise over 15 minutes. The reaction mixture was then heated at reflux and stirred for 3½ hours. The reaction mixture was then cooled to room temperature and stirred while 20 ml. of water was added portionwise. The organic layer was removed, washed with water, and dried. Evaporation of the solvent under reduced pressure provided the product as a viscous oil. The oil so formed was chromatographed over 50 g. of silica gel, eluting with benzene and ethyl acetate. Evaporation of the solvent from the combined fractions provided 580 mg. of 2-(2-cyanomethyl-5-methyl-1-cyclohexenyl)-5-n-pentyl-resorcinol as a viscous oil. M+ 313.

Analysis Calc. for $C_{20}H_{27}NO_2$ Theory: C, 76.64; H, 8.68; N, 4.47. Found: C, 76.84; H, 8.92; N, 4.25.

EXAMPLE 7

2-(2-Hydroxymethyl-5-methyl-1-cyclohexenyl)-5-(1,1-dimethylheptyl)resorcinol A solution of 1000 ml. of benzene containing 400 ml. of a seventy percent benzene solution of sodium bis(2-methoxy-ethoxy)aluminum hydride was stirred at 0°–10° C. while a suspension of 59.90 g. of 1-hydroxy-3-(1,1-dimethylheptyl-6-oxo-9-methyl-7,8,9,10-tetrahydro-6H-dibenzo[b,d]-pyran in 400 ml. of benzene was added portionwise over 1 hour. The reaction mixture was then warmed to room temperature and stirred an additional 2 hours. Again the reaction mixture was cooled to 0° C. and stirred while 1800 ml. of 20 percent aqueous hydrochloric acid solution was added. The benzene layer was separated from the aqueous acidic layer, washed with water, and dried. Evaporation of the solvent under reduced pressure provided 2-(2-hydroxymethyl-5-methyl-1-cyclohexenyl)-5-(1,1-dimethylheptyl)resorcinol as a white solid. M.P. 155°–156° C.

nmr ($CDCl_3$—$DMSO_{d6}$) δ 3.8, (s, 2H, —$CH_2O$) δ 6.25, (s, 2H, aromatic)

EXAMPLE 8

2-(2-Hydroxymethyl-5-methyl-1-cyclohexenyl)-5-(1,1-dimethylheptyl)dibenzylresorcinol A solution of 58 g. of 2-(2-hydroxymethyl-5-methyl-1-cyclohexenyl)-5-(1,1-dimethylheptyl)resorcinol in 600 ml. of ethyl alcohol containing 27.6 g. of potassium carbonate and 46.5 g. of benzyl chloride was heated at reflux and stirred for 16 hours. After cooling the reaction mixture to room temperature, 800 ml. of water was added to the mixture. The ethyl alcohol was then removed from the aqueous solution by evaporation under reduced pressure. The resulting aqueous reaction mixture was then extracted several times with diethyl ether. The ethereal extracts were combined, washed with water, and dried. Evaporation of the solvent under reduced pressure provided 63 g. of the product as a viscous oil. The product was purified by chromatography over 800 g. of silica gel, eluting with benzene and ethyl acetate. The appropriate fractions were combined and concentrated under reduced pressure, affording 51.09 g. of 2-(2-hydroxymethyl-5-methyl-1-cyclohexenyl)-5-(1,1-dimethylheptyl)dibenzylresorcinol. M+ 540.

Analysis Calc. for $C_{37}H_{48}O_3$ Theory: C, 82.18; H, 8.95. Found: C, 82.23; H, 8.77.

nmr (CDCl$_3$) δ 5.09 (s, 4H, benzyl methylenes) δ 7.40 (s, 10H, benzyl aromatic)

EXAMPLE 9

2-(2-Bromomethyl-5-methyl-1-cyclohexenyl)-5-(1,1-dimethylheptyl)dibenzylresorcinol While a solution of 27.0 g. of 2-(2-hydroxymethyl-5-methyl-1-cyclohexenyl)-5-(1,1-dimethylheptyl)dibenzylresorcinol in 50 ml. of diethyl ether was being stirred at 0° C., a solution of 16.2 g. of phosphorus tribromide in 50 ml. of diethyl ether was added dropwise over thirty minutes. The reaction mixture was then heated at reflux for one hour. After pouring the reaction mixture over 50 g. of ice, the resulting aqueous mixture was extracted with diethyl ether. The ethereal extracts were combined, washed with water, and dried. Removal of the solvent by evaporation under reduced pressure provided 28.36 g. of 2-(2-bromomethyl-5-methyl-1-cyclohexenyl)-5-(1,1-dimethylheptyl)dibenzylresorcinol as a colorless viscous oil. M+ 602, 604.

Analysis Calc. for $C_{37}H_{47}BrO_2$ Theory: C, 73.62; H, 7.85; Br, 13.24. Found: C, 73.48; H, 7.99; Br, 13.02.

nmr (CDCl$_3$) δ 5.10 (s, 4H, benzyl methylenes) δ 7.42 (s, 10H, benzyl aromatics)

EXAMPLE 10

2-(2-Cyanomethyl-5-methyl-1-cyclohexenyl)-5-(1,1-dimethylheptyl)dibenzylresorcinol To a solution of 28.0 g. of 2-(2-bromomethyl-5-methyl-1-cyclohexenyl)-5-(1,1-dimethylheptyl)dibenzylresorcinol in 125 ml. of dimethyl sulfoxide was added 4.55 g. of sodium cyanide. The reaction mixture was stirred at about 25° C. for 12 hours. The reaction mixture was then added to 1000 ml. of water, and the aqueous solution was extracted several times with diethyl ether. The ethereal extracts were combined, washed with water, and dried. Removal of the solvent by evaporation under reduced pressure provided 25 g. of the product as an oil. The oil so formed was chromatographed over 500 g. of silica gel, eluting with benzene. After combining the appropriate fractions, the solvent was removed by evaporation under reduced pressure, affording 22.69 g. of 2-(2-cyanomethyl-5-methyl-1-cyclohexenyl)-5-(1,1-dimethylheptyl)dibenzylresorcinol. M. P. 85°–86° C. M+ 549.

Analysis Calc. for $C_{38}H_{47}NO_2$ Theory: C, 83.02; H, 8.62; N, 2.55. Found: C, 82.91; H, 8.87; N, 2.50.

nmr (CDCl$_3$) δ 5.0 (s, 4H, benzyl methylenes) δ 7.35 (s, 10H, benzyl aromatics)

EXAMPLE 11

2-(2-Cyanomethyl-5-methyl-1-cyclohexenyl)-5-(1,1-dimethylheptyl)resorcinol

A solution of 8.80 g. of 2-(2-cyanomethyl-5-methyl-1-cyclohexenyl)-5-(1,1-dimethylheptyl)dibenzylresorcinol in 200 ml. of ninety-five percent aqueous ethyl alcohol was stirred at 25° C. while 440 mg. of five percent palladium suspended on charcoal was added. The reaction mixture was then stirred for seventeen hours under at hydrogen gas atmosphere at 30 psi. The reaction mixture was then filtered, and the filtrate was concentrated by evaporation of the solvent under reduced pressure, providing 5.90 g. of 2-(2-cyanomethyl-5-methyl-1-cyclohexenyl)-5-(1,1-dimethylheptyl)resorcinol. M+ 369.

Analysis Calc. for $C_{24}H_{35}NO_2$ Theory: C, 78.00; H, 9.55; N, 3.79. Found: C, 77.88; H, 9.44; N, 3.99.

nmr (CDCl$_3$) δ 6.5 (s, 2H, aromatic)

EXAMPLE 12

1-Hydroxy-3-(1,1-dimethylheptyl)-6-oxo-10-methyl-6,7,8,9,10,11-hexahydro-dibenz[b,d]oxepin A solution of 10.0 g. of 2-(2-cyanomethyl-5-methyl-1-cyclohexenyl)-5-(1,1-dimethylheptyl)dibenzylresorcinol in 100 ml. of dichloromethane was stirred at about 25° C. while a solution of 10 ml. of boron tribromide in 100 ml. of dichloromethane was added dropwise over one hour. After the addition was complete, the reaction mixture was heated at reflux and stirred for 2½ hours. The reaction mixture was then cooled and slowly added to 100 ml. of water. The aqueous mixture was extracted with dichloromethane. The organic extracts were combined, washed with water, and dried. Removal of the solvent by evaporation under reduced pressure provided the crude product as a viscous oil. The product proved to be a mixture of two products which were separated by chromatography over 200 g. of silica gel, eluting with benzene and ethyl acetate. Combining the appropriate fraction and removal of the solvent therefrom by evaporation under reduced pressure provided 580 mg. of 2-(2-cyanomethyl-5-methyl-1-cyclohexenyl)-5-(1,1-dimethylheptyl)resorcinol, and 1.26 g. of the desired product, namely 1-hydroxy-3-(1,1-dimethylheptyl)-6-oxo-10-methyl-6,7,8,9,10,11-hexahydro-dibenz[b,d]oxepin. M+ 370

Analysis Calc. for $C_{24}H_{34}O_3$ Theory: C, 77.80; H, 9.25. Found: C, 77.39; H, 9.59.

nmr (CDCl$_3$) δ 6.70 (s, 2H, aromatic)

EXAMPLE 13

2-(2-Ethoxycarbonylmethyl-5-methyl-1-cyclohexenyl)-5-(1,1-dimethylheptyl)resorcinol To a solution of 5.0 g. of 2-(2-cyanomethyl-5-methyl-1-cyclohexenyl)-5-(1,1-dimethylheptyl)resorcinol in 200 ml. of ninety-five percent aqueous ethyl alcohol was added 5 ml. of concentrated sulfuric acid. The acidic reaction mixture was heated at reflux and stirred for 5 days. An additional 5 ml. of sulfuric acid was added to the reaction mixture, and the mixture was heated at reflux and stirred for an additional 5 days. The reaction mixture was cooled to room temperature and then added to 300 ml. of water. After removal of most of the ethyl alcohol by evaporation under reduced pressure, the aqueous mixture was extracted several times with diethyl ether. The ethereal extracts were combined, washed with water, and dried. Removal of the solvent by evaporation under reduced pressure provided 3.18 g. of 2-(2-ethoxycarbonylmethyl-5-methyl-1-cyclohexenyl)-5-(1,1-dimethylheptyl)resorcinol as a viscous oil. M+ 416.

Analysis Calc. for $C_{26}H_{40}O_4$ Theory: C, 74.96; H, 9.68. Found: C, 74.70; H, 9.47.

nmr (CDCl$_3$) δ 4.15 (quartet, 2H,

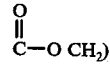

C—O CH$_2$)

δ 5.41 (s, 1H, OH) δ 5.63 (s, 1H, OH) δ 6.52 (s, 2H, aromatic)

EXAMPLE 14

2-[2-(2-Hydroxyisopropylmethyl)-5-methyl-1-cyclohexenyl]-5-(1,1-dimethylheptyl)resorcinol To a solution of 416 mg. of 2-(2-ethoxycarbonylmethyl-5-methyl-1-cyclohexenyl)-5-(1,1-dimethylheptyl)resorcinol in 25 ml. of benzene was added in one portion 5 ml. of a 3 molar solution of methyl magnesium bromide in diethyl ether. The reaction mixture was heated at reflux and stirred for 12 hours. After cooling the reaction mixture to room temperature, the mixture was poured into 10 g. of ice containing 2 ml. of concentrated sulfuric acid. The acidic aqueous mixture was then extracted several times with diethyl ether. The ethereal extracts were combined, washed with water, and dried. Removal of the solvent from the combined extracts by evaporation under reduced pressure afforded 380 mg. of 2-[2-(2-hydroxyisopropylmethyl)-5-methyl-1-cyclohexenyl]-5-(1,1-dimethylheptyl)resorcinol.

nmr (CDCl$_3$) δ 4.75 (broad s, 3H, —OH)
δ 6.45 (s, 2H, aromatic)

EXAMPLE 15

1-Hydroxy-3-(1,1-dimethylheptyl)-6,6,10-trimethyl-6,7,8,9,10,11-hexahydro-dibenz[b,d]oxepin A solution of 3.16 g. of 2-[2-(2-hydroxyisopropylmethyl)-5-methyl-1-cyclohexenyl]-5-(1,1-dimethylheptyl)resorcinol in 100 ml. of ethyl alcohol was stirred at about 25° C. while excess hydrogen chloride gas was bubbled through the solution. The reaction mixture was stirred for about 15 minutes, and then the solvent was removed by evaporation under reduced pressure, leaving an oil as the product. The oil was purified by chromatography over 100 g. of silica gel, eluting with benzene. The fractions were collected and combined, and the solvent was removed therefrom under reduced pressure to provide 2.30 g. of 1-hydroxy-3-(1,1-dimethylheptyl)-6,6,10-trimethyl-6,7,8,9,10,11-hexahydro-dibenz[b,d]oxepin. M+ 384

Analysis Calc. for $C_{26}H_{40}O_2$ Theory: C, 81.20; H, 10.48. Found: C, 81.08; H, 10.34.

nmr (CDCl$_3$) δ 4.83 (s, 1H, OH) δ 6.57 (s, 2H, aromatic)

EXAMPLE 16

2-[2-(1-Cyanoethyl)-5-methyl-1-cyclohexenyl]-5-(1,1-dimethylheptyl)dibenzylresorcinol A solution of 11.0 g. of 2-(2-cyanomethyl-5-methyl-1-cyclohexenyl)-5-(1,1-dimethylheptyl)dibenzylresorcinol in 500 ml. of benzene containing 12.5 ml. of methyl iodide was cooled in an ice-water bath and stirred while 6.75 g. of potassium tert.-butoxide was added in one portion. The reaction mixture was allowed to warm to room temperature and was then stirred for 12 hours. The reaction mixture then was poured into 1000 ml. of water, and the mixture was extracted several times with diethyl ether. The organic extracts were combined, washed with water, and dried. Removal of the solvent by evaporation under reduced pressure afforded 11.0 g. of the product as a crude oil. The oil was chromatographed over 300 g. of silica gel, eluting with benzene. The appropriate fractions were combined and concentrated under reduced pressure to afford 9.92 g. of 2-[2-(1-cyanoethyl)-5-methyl-1-cyclohexenyl]-5-(1,1-dimethylheptyl)dibenzylresorcinol as a colorless oil. M+ 563.

Analysis Calc. for $C_{39}H_{49}NO_2$ Theory: C, 83.08; H, 8.76; N, 2.48. Found: C, 83.12; H, 8.65; N, 2.41.

nmr (CDCl$_3$) δ 5.01 (s, 2H, benzyl methylene) δ 5.12 (s, 2H, benzyl methylene) δ 6.58 (s, 2H, aromatic) δ 7.41 (s, 10H, benzyl aromatic)

EXAMPLE 17

2-[2-(1-Cyanoethyl)-5-methyl-1-cyclohexenyl]-5-(1,1-dimethylheptyl)resorcinol

To a solution of 9.0 g. of 2-[2-(1-cyanoethyl)-5-methyl-1-cyclohexenyl]-5-(1,1-dimethylheptyl)dibenzylresorcinol in 200 ml. of ethyl alcohol was added 650 mg. of five percent palladium suspended on charcoal. The reaction mixture was hydrogenated at a hydrogen gas pressure of 30 psi at about 25° C. for 24 hours. The reaction mixture was then filtered, and the filtrate was concentrated to an oil by evaporation of the solvent under reduced pressure. The oil so formed was purified by chromatography over 150 g. of silica gel, eluting with benzene and ethyl acetate. Collection and combination of the appropriate fractions, followed by evaporation of the solvent under reduced pressure, provided 5.32 g. of 2-[2-(1-cyanoethyl)-5-methyl-1-cyclohexenyl]-5-(1,1-dimethylheptyl)resorcinol. M+ 383.

Analysis Calc. for $C_{25}H_{37}NO_2$ Theory: C, 78.28; H, 9.72; N, 3.65. Found: C, 78.73; H, 9.87; N, 3.46.

nmr (CDCl$_3$) 4.7 (s, 1H, OH) 4.9 (s, 1H, OH) 6.42 (m, 2H, aromatic)

EXAMPLE 18

2-[2-(1-Ethoxycarbonylethyl)-5-methyl-1-cyclohexenyl]-5-(1,1-dimethylheptyl)resorcinol A solution of 4.0 g. of 2-[2-(1-cyanoethyl)-5-methyl-1-cyclohexenyl]-5-(1,1-dimethylheptyl)resorcinol in 200 ml. of ethyl alcohol containing 10 ml. of water was stirred at 25° C. while excess hydrogen chloride gas was bubbled through the solution. The reaction mixture was then heated at reflux and stirred for 48 hours. The reaction mixture was concentrated to an oil by evaporation of the solvent under reduced pressure. The oil was then chromatographed over 150 g. of silica gel, eluting with benzene. The fraction were combined and the solvent was evaporated therefrom under reduced pressure, providing 1.67 g. of 2-[2-(1-ethoxycarbonylethyl)-5-methyl-1-cyclohexenyl]-5-(1,1-dimethylheptyl)resorcinol. M+ 430.

Analysis Calc. for $C_{27}H_{42}O_4$ Theory: C, 75.31; H, 9.83. Found: C, 75.30; H, 10.07.

nmr (CDCl$_3$) δ 4.17 (quartet, 2H,

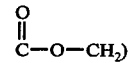

δ 6.50 (m, 2H, aromatic)

EXAMPLE 19

1-Hydroxy-3-(1,1-dimethylheptyl)-6,6,7,10-tetramethyl-6,7,8,9,10,11-hexahydro-dibenz[b,d]oxepin A solution of 1.5 g. of 2-[2-(1-ethoxycarbonyl-ethyl)-5-methyl-1-cyclohexenyl]-5-(1,1-dimethylheptyl)resorcinol in 50 ml. of benzene was rapidly added to a solution of 20 ml. of three molar methyl magnesium bromide in diethyl ether. The reaction mixture was heated at reflux and stirred for 2 hours. After cooling the mixture to room temperature, the mixture was added to 15 g. of ice and 5 ml. of concentrated sulfuric acid. The aqueous acidic solution was then extracted with diethyl ether. The ethereal extract was washed with water and dried. The solvent was then removed under reduced pressure to provide 2-[2-(1-(2-hydroxyisopropyl)ethyl)-5-methyl-1-cyclohexenyl]-5-(1,1-dimethylheptyl)resorcinol as an oil. The oil so formed was then dissolved into 10 ml. of ethyl alcohol, and excess hydrogen chloride gas was bubbled through the solution. After stirring the reaction mixture for ten minutes at room temperature, the solvent was removed under reduced pressure, leaving the product as an oil. The oil was passed through a column packed with 60 g. of silica gel, eluting with about 200 ml. of benzene. The solvent was evaporated from the combined fractions under reduced pressure to provide 1.06 g. of 1-hydroxy-3-(1,1-dimethylheptyl)-6,6,7,10-tetramethyl-6,7,8,9,10,11-hexahydro-dibenz[b,d]-oxepin. M+ 398.

Analysis Calc. for $C_{27}H_{42}O_2$ Theory: C, 81.35; H, 10.62. Found: C, 81.16; H, 10.62.

EXAMPLE 20

2-[2-(1-Cyano-1-methylethyl)-5-methyl-1-cyclohexenyl]-5-(1,1-dimethylheptyl)dibenzylresorcinol A solution comprised of 29 ml. of a 1.72 molar solution of methyl lithium in diethyl ether and 7.0 ml. of diisopropylamine in 150 ml. of diethyl ether was stirred for 30 minutes at 0° C. To the stirred reaction mixture was added a solution of 5.5 g. of 2-(2-cyanomethyl-5-methyl-1-cyclohexenyl)-5-(1,1-dimethylheptyl)dibenzylresorcinol in 50 ml. of diethyl ether. The reaction mixture was then stirred at 0° C. for 15 minutes, after which time 15.5 ml. of methyl iodide was added to the cold reaction mixture dropwise over 5 minutes. The reaction mixture was then warmed to 25° C. and was stirred for an additional 16 hours. The reaction mixture next was poured into 200 ml. of water, and the organic layer was separated therefrom. The ethereal layer was washed with 1N hydrochloric acid solution and with water. After drying the ethereal layer, the solvent was removed therefrom by evaporation under reduced pressure to provide the product as an oily residue. The product was chromatographed over 200 g. of silica gel, eluting with benzene. The fractions shown by thin layer chromatography to contain the desired product were combined and the solvent was removed therefrom to afford 4.84 g. of an oil which solidified upon standing at room temperature, providing 2-[2-(1-cyano-1-methylethyl)-5-methyl-1-cyclohexenyl]-5-(1,1-dimethylheptyl)-dibenzylresorcinol. M.P. 65°-66° C. M+ 577.

Analysis Calc. for $C_{40}H_{51}NO_2$ Theory: C, 83.14; H, 8.90; N, 2.42. Found: C, 82.84; H, 9.02; N, 2.44 nmr (CDCl$_3$) δ 5.02 (s, 2H, benzyl methylene) δ 5.05 (s, 2H, benzyl methylene) δ 6.55 (s, 2H, aromatic) δ 7.35 (m, 10H, benzyl aromatic)

EXAMPLE 21

2-[2-(1-Aminocarbonyl-1-methylethyl)-5-methyl-1-cyclohexenyl]-5-(1,1-dimethylheptyl)dibenzylresorcinol A solution of 2.0 g. of 2-[2-(1-cyano-1-methylethyl)-5-methyl-1-cyclohexenyl]-5-(1,1-dimethylheptyl)-dibenzylresorcinol in 6 ml. of ethanol containing 10 ml. of fifty percent aqueous sodium hydroxide solution was heated at reflux and stirred for 32 hours. After cooling the reaction mixture to room temperature, the excess reaction solvent was removed by evaporation under reduced pressure to provide a residue which was next dissolved in aqueous hydrochloric acid. The product was extracted from the aqueous acid solution into diethyl ether. The ethereal extracts were combined, washed with water, and dried. Removal of the solvent affered 2.0 g. of 2-[2-(1-aminocarbonyl-1-methylethyl)-5-methyl-1-cyclohexenyl]-5-(1,1-dimethylheptyl)dibenzylresorcinol as a solid. M.P. 113°-114° C. M+ 595.

Analysis Calc. for $C_{40}H_{53}NO$ Theory: C, 80.63; H, 8.97; N, 2.35. Found: C, 80.76; H, 8.66; N, 2.09.

nmr (CDCl$_3$): δ 5.02 (s, 2H, benzyl methylene) δ 5.03 (s, 2H, benzyl methylene) δ 6.55 (s, 2H, aromatic)

EXAMPLE 22

2-[2-(1-Aminocarbonyl-1-methylethyl)-5-methyl-1-cyclo hexenyl]-5-(1,1-dimethylheptyl)resorcinol A solution 5.0 g. of 2-[2-(1-aminocarbonyl-1-methylethyl)-5-methyl-1-cyclohexenyl]-5-(1,1-dimethylheptyl)-dibenzylresorcinol dissolved in 100 ml. of ethanol containing 250 mg. of five percent palladium on carbon was stirred at room temperature under hydrogen gas at a pressure of 30 psi for 26 hours. The reaction mixture then was filtered, and the filtrate was concentrated to dryness under reduced pressure to provide 3.47 g. of 2-[2-(1-aminocarbonyl-1-methylethyl)-5-methyl-1-cyclohexenyl]-5-(1,1-dimethylheptyl)resorcinol as a foam.

Analysis Calc. for $C_{26}H_{41}NO_3$ Theory: C, 75.14; H, 9.94; N, 3.37. Found: C, 75.32; H, 9.71; N, 3.17.

nmr (CDCl$_3$): δ 5.6–6.6 (broad s, 4H, NH$_2$ and OH) δ 6.4 (s, 2H, aromatic)

EXAMPLE 23

1-Hydroxy-3-(1,1-dimethylheptyl)-6-oxo-7,7,10-trimethyl-6,7,8,9,10,11-hexahydro-dibenz[b,d]oxepin Three grams of 2-[2-(1-aminocarbonyl-1-methylethyl)-5-methyl-1-cyclohexenyl]-5-(1,1-dimethylheptyl)-resorcinol was placed in a pear shaped flask and heated at 240° C. under a nitrogen gas atmosphere for 10 minutes. After cooling the material to room temperature, it was dissolved in 10 ml. of benzene, and the solution was chromatographed over 100 g. of silica gel, eluting with benzene. Combining the appropriate fractions and removal of the solvent therefrom afforded 870 mg. of 1-hydroxy-3-(1,1-dimethylheptyl)6-oxo-7,7,10-trimethyl-6,7,8,9,10,11-hexahydro-dibenz[b,d]oxepin as an oil. M+ 398.

Analysis Calc. for $C_{26}H_{38}O_3$ Theory: C, 78.35; H, 9.61. Found: C, 78.11; H, 9.93.

nmr (CDCl$_3$): δ 0.7–2.6 (m, 35H) δ 5.6 (s, 1H, OH) δ 6.6 (m, 2H, aromatic)

EXAMPLE 24

2-[2-(1-Ethoxycarbonyl-1-methylethyl)-5-methyl-1-cyclohexenyl]-5-(1,1-dimethylheptyl)resorcinol A solution of 8.24 g. of 2-[2-(1-aminocarbonyl-1-methylethyl)-5-methyl-1-cyclohexenyl]-5-(1,1-dimethylheptyl)resorcinol dissolved in 500 ml. of ethanol was stirred while anhydrous hydrogen chloride gas was added. The reaction mixture then was heated at reflux for 48 hours. The reaction mixture then was cooled to room temperature, and the solvent was removed by evaporation under reduced pressure. The reaction mixture was then dissolved in diethyl ether and washed with water, dried, and the solvent was removed under reduced pressure to provide an oil. The oil so formed was chromatographed over 250 g. of silica gel, affording 7.50 g. of 2-[2-(1-ethoxycarbonyl-1-methylethyl)-5-methyl-1-cyclohexenyl]-5-(1,1-dimethylheptyl)-resorcinol as an oil. M+ 444.

Analysis calc. for $C_{28}H_{44}O_4$ Theory: C, 75.63; H, 9.97. Found: C, 75.84; H, 9.70.

nmr (CDCl$_3$): δ 0.7–2.15 (m, 38H) δ 3.83 (q, 2H, CH$_2$) δ 5.0 (s, 1H, OH) δ 5.41 (s, 1H, OH) δ 6.43 (s, 2H, aromatic)

EXAMPLE 25

2-[2-(1-Hydroxymethyl-1-methylethyl)-5-methyl-1-cyclo hexenyl]-5-(1,1-dimethylheptyl)resorcinol A mixture of 60 ml. of a seventy percent solution of sodium bis(2-methoxyethoxy) aluminum hydride in benzene and 60 ml. of benzene was cooled to −5° C. and stirred. A solution of 7.0 g. of 2-[2-(1-ethoxycarbonyl-1-methylethyl)-5-methyl-1-cyclohexenyl]-5-(1,1-dimethylheptyl)resorcinol dissolved in 50 ml. of benzene was added to the reaction mixture dropwise over 10 minutes. The reaction mixture than was warmed to room temperature and stirred for 3 hours. After cooling the reaction mixture again to 0° C., 500 ml. of aqueous hydrochloric acid was added, and the product was extracted from the aqueous acid solution into diethyl ether. The ethereal extracts were combined, washed with water, dried, and concentrated under reduced pressure to provide a glassy residue. The residue was chromatographed over 160 g. of silica gel, eluting with 1 percent ethyl acetate in benzene. Combining the appropriate fractions and evaporation of the solvent therefrom afforded 5.41 g. of 2-[2-(1-hydroxymethyl-1-methylethyl)-5-methyl-1-cyclohexenyl]-5-(1,1-dimethylheptyl)resorcinol as an oil. M+ 402.

Analysis Calc. for $C_{26}H_{42}O_3$ Theory: C, 77.56; H, 10.52. Found: C, 77.75; H, 10.54.

nmr (CDCl$_3$): 67 5.75–6.5 (m, 3H, OH) δ 6.4 (s, 2H, aromatic)

EXAMPLE 26

1-Hydroxy-3-(1,1-dimethylheptyl)-7,7,10-trimethyl-6,7,8,9,10,11-hexahydro-dibenz[b,d]oxepin A mixture of 4.50 g. of 2-[2-(1-hydroxymethyl-1-methylethyl)-5-methyl-1-cyclohexenyl]-5-(1,1-dimethylheptyl)resorcinol and 2.60 g of N,N'-dicyclohexylcarbodiimide was heated at 110° C. and stirred for 3 hours. The mixture was then cooled to room temperature, dissolved in 15 ml. of benzene, and filtered. The filtrate was chromatographed over 250 g. of silica gel, eluting with benzene. Collection of the appropriate fractions and removal of the solvent therefrom under reduced pressure provided 2.12 g. of 1-hydroxy-3-(1,1-dimethylheptyl)-7,7,10-trimethyl-6,7,8,9,10,11-hexahydro-dibenz[b,d]oxepin. M+ 384.

Analysis Calc. for $C_{26}H_{40}O_2$ Theory: C, 81.20; H, 10.48. Found: C, 81.72; H, 9.77.

nmr (CDCl$_3$): δ 0.8–2.4 (m, 35H) δ 3.3 (s, 2H, CH$_2$O) δ 6.22 (s, 2H, aromatic)

EXAMPLE 27

2-[2-(2-Hydroxyethyl)-5-methyl-1-cyclohexenyl]-5-(1,1-dimethylheptyl)resorcinol

A solution containg 86.6 g. of a seventy percent solution of sodium bis(2-methoxyethoxy)aluminum hydride in 120 ml. of benzene was stirred in an ice-water bath while a solution of 11.30 g. of 2-(2-ethoxycarbonylmethyl-5-methyl-1-cyclohexenyl)-5-(1,1-dimethylheptyl)-resorcinol dissolved in 100 ml. of benzene was added to the reaction mixture dropwise over 15 minutes. The reaction mixture was then warmed to 25° C. and stirred for 1 hour. After cooling the reaction mixture again to 0° C., 1000 ml. of aqueous hydrochloric acid was added. The aqueous acid solution was extracted with diethyl ether, and the ethereal extracts were combined, washed with water, and dried. Evaporation of the solvent under reduced pressure afforded 10.15 g. of 2-[2-(2-hydroxyethyl)-5-methyl-1-cyclohexenyl]-5-(1,1-dimethylheptyl)-resorcinol as an oil which solidified after standing at room temperature. M.P. 83°–86° C. M+ 374.

Analysis Calc. for $C_{24}H_{38}O_3$ Theory: C, 76.96; H, 10.23. Found: C, 77.20; H, 9.01.

nmr (CDCl$_3$): δ 0.8–2.4 (m, 33H) δ 5.75–6.5 (m, 4H)

EXAMPLE 28

2-[2-(2-Bromomethyl)-5-methyl-1-cyclohexenyl]-5-(1,1-dimethylheptyl)resorcinol

A solution of 3.0 g. of 2-[2-(2-hydroxyethyl)-5-methyl-1-cyclohexenyl]-5-(1,1-dimethylheptyl)resorcinol dissolved in 50 ml. of diethyl ether was cooled in an ice-water bath and stirred while a solution of 3.0 ml. of phosphorous tribromide dissolved in 50 ml. of diethyl ether was added dropwise over 15 minutes. The reaction mixture was then warmed to room temperature and stirred for four hours, and next was heated at reflux and stirred for an additional 1 hour. The reaction mixture was poured into 250 ml. of ice water, and the product was extracted from the aqueous reaction mixture into diethyl ether. The ethereal extracts were combined, washed with water, and concentrated under reduced pressure to provide 3.53 g. of 2-[2-(2-bromoethyl)-5-methyl-1-cyclohexenyl]-5-(1,1-dimethylheptyl)resorcinol.

Analysis Calc. for $C_{24}H_{37}O_2Br$ Theory: C, 65.89; H, 8.53; Br, 18.27. Found: C, 64.37; H, 6.49; Br, 14.05.

nmr (CDCl$_3$): δ 6.8 (s, 2H, aromatic) δ 7.85 (s, 2H, OH)

EXAMPLE 29

1-Hydroxy-3-(1,1-dimethylheptyl)-10-methyl-6,7,8,9,10,11-hexahydro-dibenz[b,d]oxepin A mixture of 2.65 g. of 2-[2-(2-hydroxyethyl)-5-methyl-1-cyclohexenyl]-5-(1,1-dimethylheptyl)resorcinol and 1.65 g. of N,N'-dicyclohexylcarbodiimate was heated at 110° C. and stirred for two hours. The reaction mixture was cooled to room temperature and then suspended in 25 ml. of benzene, and filtered. Chromatography of the filtrate over 130 g. of silica gel provided 1.29 g. of 1-hydroxy-3-(1,1-dimethylheptyl)-10-methyl-6,7,8,9,10,11-hexahydro-dibenz[b,d]oxepin as a white solid. M.P. 134°–136° C. M+ 356.

Analysis Calc. for $C_{24}H_{36}O_2$ Theory: C, 80.85; H, 10.18. Found: C, 80.99; H, 9.81.

nmr (CDCl$_3$): δ 0.7–2.8 (m, 31H) δ 4.4 (triplet, 2H) δ 4.97 (s, 1H, OH) δ 6.5 (m, 2H, aromatic)

EXAMPLE 30

1-Hydroxy-3-(1,1-dimethylheptyl)-10-methyl-6,7,8,9,10,11-hexahydro-dibenz[b,d]oxepin A solution of 3.5 g. of 2-[2-(2-bromomethyl)-5-methyl-1-cyclohexenyl]-5-(1,1-dimethylheptyl)resorcinol in 200 ml. of acetone containing 4.4 g. of potassium carbonate was heated at reflux and stirred for forty-eight hours. The reaction mixture was cooled to room temperature and then concentrated by evaporation under reduced pressure, thus providing 2.2 g. of 1-hydroxy-3-(1,1-dimethylheptyl)-10-methyl-6,7,8,9,10,11-hexahydro-dibenz[b,d]oxepin. M+ 356.

Analysis Calc. for $C_{24}H_{36}O_2$ Theory: C, 80.85; H, 10.18. Found: C, 80.13; H, 9.42.

EXAMPLE 31

2-(2-Hydroxycarbonylmethyl-5-methyl-1-cyclohexenyl)-5-(1,1-dimethylheptyl)dibenzylresorcinol A solution of 10.0 g. of 2-(2-cyanomethyl-5-methyl-1-cyclohexenyl)-5-(1,1-dimethylheptyl)dibenzylresorcinol in 3 ml. of ethanol containing 50 ml. of 50 percent aqueous sodium hydroxide was heated at reflux and stirred for 16 hours. After cooling the reaction mixture to room temperature, the excess ethanol was removed therefrom by evaporation under reduced pressure, and then 250 ml. of water was added to the reaction mixture. After acidifying the aqueous reaction mixture to pH 1 by the addition of concentrated hydrochloric acid, the mixture was extracted with diethyl ether. The ethereal extracts then were combined, washed with water, and dried. Evaporation of the solvent under reduced pressure afforded 8.2 g. of 2-(2-hydroxycarbonylmethyl-5-methyl-1-cyclohexenyl)-5-(1,1-dimethylheptyl)dibenzylresorcinol as a white solid. M.P. 69°–70° C. M+ 568.

Analysis Calc. for $C_{38}H_{48}O_4$ Theory: C, 80.24; H, 8.51. Found: C, 80.16; H, 8.35.

nmr (CDCl$_3$): δ 0.7–2.4 (m, 29H) δ 2.8 (s, 2H, CH$_2$) δ 4.98 (s, 4H, benzyl methylenes) δ 6.5 (s, 2H, aromatic) δ 7.25 (s, 10H, benzyl aromatic)

EXAMPLE 32

2-(2-Hydroxycarbonylmethyl-5-methyl-1-cyclohexenyl)-5-(1,1-dimethylheptyl)resorcinol A solution of 7.0 g. of 2-(2-hydroxycarbonylmethyl-5-methyl-1-cyclohexenyl)-5-(1,1-dimethylheptyl)dibenzylresorcinol in 150 ml. of ethanol containing 800 mg. of five percent palladium on charcoal was stirred under hydrogen gas at 40 p.s.i. for 24 hours at room temperature. The reaction mixture then was filtered and the filtrate was concentrated to dryness by evaporation under reduced pressure to provide 4.80 g. of 2-(2-hydroxycarbonylmethyl-5-methyl-1-cyclohexenyl)-5-(1,1-dimethylheptyl)-resorcinol as a glass. M+ 388.

Analysis Calc. for $C_{24}H_{36}O_4$ Theory: C, 74.19; H, 9.34. Found: C, 74.11; h, 9.28.

nmr (CDCl$_3$): δ 0.7–2.4 (m, 29H) δ 2.95 (s, 2H, CH$_2$) δ 6.4 (s, 2H, aromatic) δ 7.05 (s, 3H, COOH and OH)

EXAMPLE 33

1-hydroxy-3-(1,1-dimethylheptyl)-6-oxo-10-methyl-6,7,8,9,10,11-hexahydro-dibenz[b,d]oxepin A solution containing 3.5 g. of 2-(2-hydroxycarbonylmethyl-5-methyl-1-cyclohexenyl)-5-(1,1-dimethylheptyl)resorcinol in 35 ml. of dichloromethane was added dropwise over 15 minutes to a stirred solution of 2.19 g. of N,N'-dicyclohexylcarbodiimide in 50 ml. of dichloromethane. After the addition was completed, the reaction mixture was stirred for 1 hour at room temperature. The reaction mixture then was filtered and the filtrate was concentrated by evaporation of the solvent under reduced pressure to provide a glassy residue. The residue so formed was chromatographed over 100 g. of silica gel, eluting with benzene. Combining the appropriate fractions and removal of the solvent therefrom by evaporation under reduced pressure afforded 2.55 g. of 1-hydroxy-3-(1,1-dimethylheptyl)-6-oxo-10-methyl-6,7,8,9,10,11-hexahydro-dibenz[b,d]oxepin. M+ 370.

Analysis Calc. for $C_{24}H_{34}O_3$ Theory: C, 77.80; H, 9.25. Found: C, 77.53; H, 9.04.

nmr (CDCl$_3$): δ 0.6–2.6 (m, 29H) δ 2.89 (s, 2H, C$_7$ methylene) δ 6.2 (2s, 1H, OH) δ 6.61 (s, 2H, aromatic)

I claim:

1. A compound of the formula

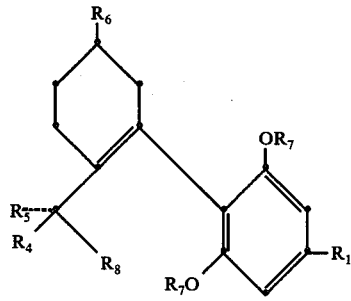

wherein:
$R_1$ is $C_5$–$C_{10}$ alkyl;
$R_4$ and $R_5$ independantly are hydrogen or methyl;
$R_6$ is $C_1$–$C_4$ alkyl;
$R_7$ is hydrogen or benzyl; and
$R_8$ is selected from the group consisting of chloro, bromo, cyano, chloromethyl, bromomethyl, $C_1$–$C_3$ alkoxycarbonyl, hydroxycarbonyl, aminocarbonyl, aminomethyl, subject to the limitations that when $R_8$ is aminocarbonyl, $R_4$ and $R_5$ are other than hydrogen, and when $R_8$ is chloro or bromo, $R_4$ and $R_5$ are other than methyl.

2. The compound of claim 1 wherein $R_4$ and $R_5$ are hydrogen, $R_7$ is benzyl, and $R_8$ is cyano.

3. The compound of claim 2, said compound being 2-(2-cyanomethyl-5-methyl-1-cyclohexenyl)-5-(1,1-dimethyl-heptyl)dibenzylresorcinol.

4. The compound of claim 1 wherein $R_4$ is hydrogen, $R_5$ is methyl, and $R_8$ is cyano.

5. The compound of claim 1 wherein $R_4$ and $R_5$ both are methyl and $R_8$ is cyano.

* * * * *